United States Patent
Kohler et al.

(10) Patent No.: US 7,883,729 B2
(45) Date of Patent: Feb. 8, 2011

(54) NATURAL VEGETABLE OIL CONCENTRATED IN UNSAPONIFIABLE MATTERS AS FOOD INGREDIENT

(75) Inventors: Carole Kohler, Paris (FR); Philippe Msika, Paris (FR); Antoine Piccirilli, Versailles (FR)

(73) Assignee: Laboratories Expanscience, Courbevoie (FR)

( * ) Notice: Subject to any disclaimer, the term of this patent is extended or adjusted under 35 U.S.C. 154(b) by 0 days.

(21) Appl. No.: 10/239,298

(22) PCT Filed: Mar. 19, 2001

(86) PCT No.: PCT/FR01/00814

§ 371 (c)(1),
(2), (4) Date: Dec. 18, 2002

(87) PCT Pub. No.: WO01/70046

PCT Pub. Date: Sep. 27, 2001

(65) Prior Publication Data

US 2003/0108650 A1    Jun. 12, 2003

(30) Foreign Application Priority Data

Mar. 20, 2000    (FR) ................................. 00 03522

(51) Int. Cl.
*A61K 36/28* (2006.01)
*A61K 36/00* (2006.01)

(52) U.S. Cl. ........................ 424/764; 424/725; 424/776; 514/458; 426/601

(58) Field of Classification Search .................. None
See application file for complete search history.

(56) References Cited

U.S. PATENT DOCUMENTS

| 6,146,616 A | 11/2000 | Msika et al. |
| 2004/0013753 A1 | 1/2004 | Boumediene et al. |
| 2004/0018257 A1 | 1/2004 | Boumediene et al. |

FOREIGN PATENT DOCUMENTS

| DE | 196 52 522 | * | 6/1998 |
| EP | 0 785 249 A | | 7/1997 |
| WO | WO 80 02100 A | | 10/1980 |
| WO | WO 98 18888 A | | 5/1998 |
| WO | WO 99/63031 | * | 12/1999 |
| WO | WO 00 49116 A | | 8/2000 |

OTHER PUBLICATIONS

Hollo et al. Tests For The Deacidification of Sunflower Oil Through Molecular Distillation; Fats, Soaps, Paints; Organ of the German Society for Fat Science in Association with the magazine Foodstuffs Industry; vol. 66, Iss. 11 (1964) pp. 1-22 translation.*

Reynolds, T. Antioxidants and Cancer: What is The Evidence? Journal of the National Cancer Institute, Jul. 5, 2000, vol. 92, Issue 13 pp. 1-3 from ProQuest internet site.*

The Heart OUtcomes Prevention Evaluation Study Investigators; Vitamin e Supplementation and Cardiovascular Events in High-Risk Patients; The New England Journal of Medicine; Jan. 20, 2000, vol. 342, Issue 3, pp. 1-7 from ProQuest direct internet site.*

Ghosh et al. Isolation of Tocopherol and Sterol Concentrate From Sunflower Oil Deodorizer Distillate; JAOCS, (1996) vol. 73, No. 10, pp. 1271-1274.*

Ooi et al., "Recovery of Carotenoids from Palm Oil" *Journal of the American Oil Chemists' Society,* American Oil Chemists' Society Champaign, US. Apr. 1994, vol. 71, No. 4, pp. 423-426.

Teoh, M.K. et al., "Protection by tocotrienols against hypercholesterolaemia and atheroma," Med. J. Malaysia, Sep. 1994; 49(3), pp. 255-262. (Abstract).

Giugliano, "Dietary antioxidants for cardiovascular prevention," Nutr. Metab. Cardiovasc. Dis., Feb. 2000; 10(1), pp. 38-44. (Abstract).

Ziouzenkova et al., "Oxidative stress resulting from hemolysis and formation of catalytically active hemoglobin: protective strategies," Int. J. Clin. Pharmacol. Ther., Mar. 1999; 37(3), pp. 125-132. (Abstract).

Ginter, "Cardiovascular disease prevention in eastern Europe," May 1998; 14(5), pp. 452-457. (Abstract).

McVean et al., "Prevention of DNA photodamage by vitamin E compounds and sunscreens: roles of ultraviolet absorbance and cellular uptake," Mol. Carcinog, Mar. 1999; 24(3), pp. 169-176. (Abstract).

Gehring et al., "Influence of vitamin E acetate on stratum corneum hydration," Arzneimittelforschung, Jul. 1998; 48(7), pp. 772-775. (Abstract).

Trevithick et al., "Topical tocopherol acetate reduces post-UVB, sunburn-associated erythema, edema, and skin sensitivity in hairless mice," Arch. Biochem. Biophys., Aug. 1992; 1;296(2), pp. 57582. (Abstract).

Lopez-Torres et al., "Topical application of alpha-tocopherol modulates the antioxidant network and diminishes ultravioletinduced oxidative damage in murine skin," Br. J. Dennatol., Feb. 1998; 138(2), pp. 207-215. (Abstract).

* cited by examiner

*Primary Examiner*—Patricia Leith
(74) *Attorney, Agent, or Firm*—Foley & Lardner LLP

(57) ABSTRACT

The invention concerns a natural vegetable oil selected among palm oil, corn germ oil, sunflower oil and canola oil, concentrated in unsaponifiable matters, such that said oil unsaponifiable matter content is 3 to 15% m/m. Said concentrated natural vegetable oil constitutes a novel food ingredient enriched in particular in vitamin E and phytosterol, useful as favored food source in vitamin E and phytosterol, meeting recommended daily intake.

6 Claims, No Drawings

NATURAL VEGETABLE OIL CONCENTRATED IN UNSAPONIFIABLE MATTERS AS FOOD INGREDIENT

The present invention relates to a natural plant oil concentrated in its unsaponifiable fraction, as a food ingredient, to a food composition or a food supplement comprising said concentrated plant oil, and to a process for preparing this oil.

Plant oils and food compositions or food supplements comprising these concentrated plant oils are used, for the purposes of the present invention, for dietary, nutritional and cosmetic purposes.

The present invention also relates to an oral cosmetic treatment method, in particular for improving the appearance of the skin.

The problem posed by the present invention is that of proposing a novel food or food ingredient enriched in unsaponifiable constituents and especially in vitamin E and phytosterols, while maintaining a supply of monounsaturated fatty acids and of essential polyunsaturated fatty acids that is comparable with the supply of these compounds in products of this type (standard oils), this enriched food thus enabling the overall calorific supply to be reduced.

Oils generally supplemented with vitamin E are commercially available, as are food compositions generally known as "functional foods" supplemented with phytosterols, or alternatively with beta-carotene.

However, the molecules supplied as supplement: vitamin E, phytosterols, beta-carotene, etc., are obtained by chemical purification from an external source such as the released products of deodorization (by-products of the oil refining industry) and tall oil (by-product of the paper pulp industry).

The inventors of the present patent application are proposing a natural plant oil chosen from palm oil, corn germ oil, sunflower oil and rapeseed oil, concentrated in unsaponifiable fraction, as a food ingredient. This oil may be obtained according to a process that is novel relative to the prior art since it consists in concentrating the nutrients by means of a physical process rather than by supplying nutrients from a chemically obtained external source.

In the context of the present invention, the term "palm oil" means palm oil not obtained especially by demargarination of palm olein, obtained especially by demargarination of palm oil.

It has now been found by the Applicant that the concentrated natural plant oil according to the present invention allows this problem to be overcome.

The concentrated natural plant oil according to the invention also has the following advantages: it reduces the risk of atherogenesis, it has hypocholesterolemiant properties, it acts in the prevention of certain cancers and cardiovascular diseases, in stimulating the immune response in the elderly, in reducing the risk of cataracts and in retarding the progress of neurovegetative diseases.

Another advantage of the concentrated natural plant oil according to the present invention is that it can be used in cosmetics ("food-cosmetic"), more particularly in order to improve the appearance of the skin, to moisturize the skin, to maintain the skin barrier and the intercorneocyte cement by means of supplying essential fatty acids and sterols, in order to prevent aging of the skin by trapping free radicals, and as an anti-inflammatory agent.

The subject of the present invention is a natural plant oil chosen from palm oil, corn germ oil, sunflower oil and rapeseed oil, concentrated in unsaponifiable material, as a food ingredient, such that the content of unsaponifiable fraction in this oil is 3% to 15% m/m. The term "natural" plant oil means an oil whose plant source has not been genetically modified.

For the purposes of the present patent application, the term "food ingredient" means that the natural plant oil concentrated in unsaponifiable material is incorporated either into a food composition or into a food supplement. The term "food ingredient" is especially not aimed at "table oil" as a food of major consumption.

In the context of the present invention, the food composition can take any form of food usually containing oil, such as, for example, the form of biscuits, salad dressing, etc. Said food composition may then contain between 5% and 50% by weight of concentrated plant oil according to the present invention.

The food supplement may be in the form of the oil as directly obtained by the process for enriching in unsaponifiable material as described below, or in the form of gel capsules or soft gelatin or plant capsules in the context of the present invention. Said food supplement may then contain from 10% to 100% by weight of concentrated plant oil according to the present invention.

More particularly, the unsaponifiable fraction of the concentrated natural plant oil according to the present invention is composed of 0.3% to 2.5% tocopherol and 1.3% to 8% phytosterol by weight.

Even more particularly, said unsaponifiable fraction of this concentrated plant oil contains:

from 0.2% to 10% by mass of sterols, triterpene alcohols and methylsterols,
from 0.1% to 2% by mass of total tocopherols and tocotrienols,
from 0.1% to 7% by mass of squalene,
from 0.1% to 1% by mass of carotenes.

The present invention relates especially to palm olein concentrated in unsaponifiable material as a food ingredient, characterized in that the content of unsaponifiable material ranges from 4.5% to 5.5%, including 1% to 2% tocotrienols, 0.4% to 0.6% tocopherols, 0.1% to 0.3% carotenes and 1% to 4% phytosterols.

Typically, the palm olein concentrated in unsaponifiable material is composed on average of 95% fatty acids in the form of triglycerides, 5% unsaponifiable material including 1.5% tocotrienols, 0.5% tocopherols, 0.2% carotenes and 1.5% phytosterols.

This palm olein concentrated in unsaponifiable material is substantially equivalent to palm olein (source) for the supplies of palmitic acid (C 16:0) and of oleic acid (C 18:1 n-9).

It has the nutritional benefit of being a preferred source of tocotrienols, the antioxidant role of which is nowadays known. It is also a food source concentrated in vitamin E, covering the Recommended Daily Intake (R.D.I.).

For example, a daily dose of said palm olein concentrated in unsaponifiable material, set at between 1 and 3 g, supplies 6 to 25 mg of vitamin E, 200 to 900 Retinol Equivalent (vitamin A in the form of provitamin A) and 15 to 45 mg of total phytosterols.

Palm olein thus concentrated in unsaponifiable material is an additional source of supply of vitamin E and provitamin A; it does not in any way replace an existing food. This concentrated palm olein may be used as a food ingredient, at doses of between 1 and 3 g per day and per person, allowing a nutritional reequilibration of the supplies of vitamin E, provitamin A and phytosterols in various food products or in functional foods.

In addition, the present invention relates to corn germ oil concentrated in unsaponifiable material, as a food ingredient, characterized in that the content of unsaponifiable material ranges from 9% to 11%, including 6% to 8% phytosterols and 1% to 3% tocopherols.

Typically, the corn germ oil concentrated in unsaponifiable material is composed on average of 90% fatty acid in the form of triglycerides, and 10% unsaponifiable materials including 7% phytosterols and 2% tocopherols.

Nutritionally, the corn germ oil concentrated in unsaponifiable material is substantially equivalent to corn germ oil (source) for the supplies of essential linoleic acid (C18:2 n-6) and oleic acid (C18:1 n-9).

It is a food source concentrated in vitamin E, covering the Recommended Daily Intake (R.D.I.). It also has the nutritional benefit of being a preferred source of phytosterols, the hypocholesterolemiant role of which is nowadays known.

For example, a daily dose of said concentrated corn germ oil set at between 2 and 8 g supplies 11 to 45 mg of vitamin E and 140 to 560 mg of total phytosterols.

The corn germ oil thus concentrated in unsaponifiable material is an additional source of supply of vitamin E and phytosterols; it does not in any way replace an existing food.

This concentrated corn germ oil may be used as a food ingredient, at doses of between 2 and 8 g per day and per person, allowing a nutritional reequilibration of the supplies of vitamin E and of phytosterols in various food products or in functional foods.

The present invention also relates to sunflower oil concentrated in unsaponifiable material, as a food ingredient, characterized in that the content of unsaponifiable material ranges from 6% to 8%, including 4% to 7% phytosterols and 0.5% to 1.5% tocopherols.

Typically, the sunflower oil concentrated in unsaponifiable material is composed on average of 93% fatty acid in the form of triglyerides, and 7% unsaponifiable material including 5% phytosterols and 1% tocopherols.

Nutritionally, the sunflower oil concentrated in unsaponifiable material is substantially equivalent to sunflower oil (source) for the supplies of essential linoleic acid (C18:2 n-6) and oleic acid (C18:1 n-9).

It is a food source concentrated in vitamin E, covering the Recommended Daily Intake (R.D.I.). It also has the nutritional benefit of being a preferred source of phytosterols, the hypocholesterolemiant role of which is nowadays known For example, a daily dose of said concentrated sunflower oil set at between 1.5 and 5 g supplies 10 to 45 mg of vitamin E and 75 to 250 mg of total phytosterols.

The sunflower oil thus concentrated in unsaponifiable material is an additional source of supply of vitamin E and of phytosterols; it does not in any way replace an existing food.

This concentrated sunflower oil may be used as a food ingredient, at contents of between 1.5 and 5 g per day and per person, allowing a nutritional reequilibration of the supplies of vitamin E and of phytosterols in various food products or in functional foods.

Finally, the present invention relates to rapeseed oil concentrated in unsaponifiable material, as a food ingredient, since the content of unsaponifiable material ranges from 8% to 10% unsaponifiable material, including 6% to 8% phytosterols and 0.5% to 1.5% tocopherols.

Typically, the rapeseed oil [lacuna] in unsaponifiable material is composed on average of 91% fatty acid in the form of triglycerides, and 9% unsaponifiable material including 7% phytosterols and 1% tocopherols.

Nutritionally, the rapeseed oil concentrated in unsaponifiable material is substantially equivalent to rapeseed oil (source) for the supplies of essential linoleic acid (C18:2 n-6) and linolenic acid (C18:3 n-9).

It is a food source concentrated in vitamin E, covering the Recommended Daily Intake (R.D.I.). It also has the nutritional benefit of being a preferred source of phytosterols, the hypocholesterolemiant role of which is nowadays known.

For example, a daily dose of said concentrated rapeseed oil set at between 1.5 and 5 g supplies 3 to 20 mg of vitamin E (3 to 20 mg α-T.E.) and 105 to 350 mg of total phytosterols.

The rapeseed oil thus concentrated in unsaponifiable material is an additional source of supply of vitamin E and of phytosterols: it does not in any way replace an existing food.

This rapeseed oil concentrated in unsaponifiable material may be used as a food ingredient, at contents of between 1.5 and 5 g per day and per person, allowing a nutritional reequilibration of the supplies of vitamin E and of phytosterols in various food products or in functional foods.

The present invention also relates to a process for preparing natural plant oil chosen from palm oil, corn germ oil, sunflower oil and rapeseed oil, concentrated in unsaponifiable material according to the invention, comprising at least one step of molecular distillation of the plant oil before concentration under the following conditions:
temperature from 200° C. to 280° C.,
pressure from $10^{-3}$ to $10^{-2}$ mmHg.

In addition, the present invention involves the use of a natural plant oil concentrated in unsaponifiable material according to the invention or obtained by the process according to the invention, for the preparation of a food ingredient for the purpose of supplying essential monounsaturated and polyunsaturated fatty acids and for reducing the overall calorific intake, and also for the purpose of improving the appearance of the skin, in order to prevent aging of the skin by trapping free radicals, and/or as an anti-inflammatory agent and also as a hypocholesterolemiant, as an agent acting in the prevention of atherogenesis, cancers, cardiovascular diseases, as an agent for stimulating the immune response in the elderly, as an agent for reducing the risk of cataracts or as an agent for retarding the progress of neurovegetative diseases.

The oral cosmetic treatment method for improving the appearance of the skin and for preventing aging of the skin, photoaging and photoimmunosuppression, by trapping free radicals, characterized in that it involves the ingestion of a concentrated natural plant oil according to the invention, also forms part of the invention.

The present invention also relates to a food ingredient, characterized in that it contains a natural plant oil chosen from palm oil, corn germ oil, sunflower oil and rapeseed oil, concentrated in unsaponifiable material such that the content of unsaponifiable fraction of this oil is from 5% to 12% m/m.

More particularly, the unsaponifiable fraction of the concentrated natural plant oil included in the food ingredient according to the present invention is composed of 0.3% to 2.5% tocopherol and 1.3% to 8% phytosterols by weight.

Even more particularly, this food ingredient is such that said unsaponifiable fraction of this concentrated plant oil contains:
from 0.2% to 10% by mass of sterols, triterpene alcohols and methylsterols,
from 0.1% to 2% by mass of total tocopherols and tocotrienols,
from 0.1% to 7% by mass of squalene,
from 0.1% to 1% by mass of carotenes.

Preferably, the food composition, in the form in which the food ingredient may be found, contains from 0.5% to 20% by mass of a natural plant oil chosen from palm oil, corn germ oil, sunflower oil and rapeseed oil, concentrated in unsaponifiable material, relative to the total mass of the food composition.

Advantageously, this food ingredient is used to improve the appearance of the skin and/or to prevent aging of the skin, photoaging and photoimmunosuppression, by trapping free radicals, as an anti-inflammatory agent, as a hypocholesterolemiant agent, as an agent for preventing atherogenesis, cancers and cardiovascular diseases, as an agent for stimulating the immune response in the elderly, as an agent for reducing the risk of cataracts or as an agent for retarding the progress of neurovegetative diseases.

A subject of the present invention is also a cosmetic treatment method such that it comprises the ingestion of natural plant oil chosen from palm oil, corn germ oil, sunflower oil and rapeseed oil, concentrated in unsaponifiable material, as a food ingredient or the oral administration of a food ingredient containing a natural plant oil chosen from palm olein, corn germ oil, sunflower oil and rapeseed oil, concentrated in unsaponifiable material.

The unsaponifiable fraction of a food plant oil is defined as all of the constituents which, after saponification (basic hydrolysis), are very sparingly soluble in water and soluble in solvents known as "fat solvents" such as, for example, alkanes, chlorinated alkanes and ethers.

The proportion of unsaponifiable material contained in a fatty substance quite clearly depends on the biological origin of this fatty substance, on the treatments that it may have undergone (refining) and also on the nature of the extraction solvent (diethyl ether, hexane).

In general, the unsaponifiable fraction of a plant oil may comprise the following constituents: sterols and methylsterols, tocopherols (vitamin E) and tocotrienols, carotenes (provitamin A), other terpene compounds (triterpene alcohols), waxes and fatty alcohols, saturated and unsaturated aliphatic hydrocarbons, and squalene.

On average, the natural plant oils chosen from palm oil, corn germ oil, sunflower oil and rapeseed oil, concentrated in unsaponifiable materials, have unsaponifiable material contents of between 0.5% and 1.5%. The various constituents of the unsaponifiable material from the plant oils all have molecular masses less than those of triglycerides. It is thus possible to separate these compounds from glycerides, at least partially, in order to obtain a plant oil concentrated in unsaponifiable material.

The natural plant oil chosen from palm oil, corn germ oil, sunflower oil and rapeseed oil, concentrated in unsaponifiable material according to the present invention, may advantageously be obtained by molecular distillation.

Molecular distillation (or short-path distillation) is a physical process of fractional evaporation carried out under high vacuum ($10^{-2}$ to $10^{-3}$ mmHg) and at high temperature (200-300° C.). This technique is particularly suitable for the distillation of heat-sensitive compounds, of high molecular weights and of low volatility (phytosterols, natural vitamins, oils and fatty substances, flavorings, etc.).

In practical terms, the molecular distillation is carried out in distillation devices of centrifugal type with rotating plates or of scraped-film type.

This process makes it possible especially to perform separation, purification, decolorization and deodorization operations. This technique is recognized as a means of physical purification that may be used in the flavorings and ingredients industry (e.g. purification of natural vitamin E).

When applied to plant oils, molecular distillation makes it possible preferentially to extract the lightest compounds of which they are made (unsaponifiable fraction). Specifically, under a high vacuum and at a suitable temperature, the unsaponifiable fraction is vaporized and then recondensed, thus constituting the distillate.

In the case of the distillation of a natural plant oil, the distillate is known as a "plant oil concentrated in unsaponifiable material"; this distillate has been concentrated in unsaponifiable material from the source oil. The content of unsaponifiable material in the concentrated plant oil may be up to 10 times the content of unsaponifiable material in the corresponding source oil.

This enrichment in unsaponifiable material corresponds to a partial removal of the triglycerides.

It has also been confirmed that this process does not result in any chemical change or impairment of the compounds of the unsaponifiable material, and that the highly unsaturated fractions were preserved. Consequently, the fatty acid distribution of the concentrated plant oil is identical to that of the plant oil before concentration.

Preferably, the concentrated natural plant oil according to the present invention is obtained by molecular distillation of the corresponding plant oil under the following conditions: temperature from 200 to 280° C., pressure from $10^{-3}$ to $10^{-2}$ mmHg.

As mentioned previously, the nutritional properties of the food ingredient according to the invention are defined as regards: the constituent fatty acids, especially linoleic acid C18:2 (n-6) and linolenic acid C18:3 (n-3), but also oleic acid C18:1 (n-9), its vitamin E content and its phytosterol, squalene and carotene content.

Oleic acid

Recent nutritional studies, performed in particular on olive oil (Mediterranean diet), have shown the role of oleic acid in the metabolism of the circulating cholesterol via the LDL and HDL lipoproteins.

Oleic acid leads to a reduction in the LDL-cholesterol, coupled with an increase in the HDL-cholesterol, resulting in an effect of reducing the risk of atherogenesis. Oleic acid thus participates in protecting against cardiovascular diseases.

Thus, the food ingredient according to the invention contributes toward a supply of monounsaturated fatty acids, via oleic acid.

Linoleic acid

A very large number of nutritional studies have been performed to show the essential role of this fatty acid.

Linoleic acid C18:2 (n-6) is an "essential" fatty acid, i.e. our body does not know how to synthesize it from other fatty acids. It is the precursor (or lead member) of the metabolic series of the polyunsaturated fatty acids known as n-6 or $\overline{\omega}$ 6, which are also "essential" fatty acids on account of their vital functions for the body.

This series of fatty acids comprises, inter alia, arachidonic acid C20:4 which is the basis of the synthesis of eicosanoids (prostaglandins, thromboxanes and leukotrienes). Eicosanoids are molecules with high biological activity, known as oxygenated chemical mediators which are involved in the mechanism of platelet aggregation. Eicosanoids are also involved in controlling platelet aggregation (type I prostaglandin—or PG I—and thromboxane A—or TX A), controlling renal function (PG E and PG F) and inflammatory and immune phenomena (type B leukotrienes—or LT B).

Linoleic acid acts as a hypocholesterolemiant.

Besides their metabolic role, linoleic acid and the unsaturated fatty acids of the series (n-6) play a structural role in cell membranes and are involved in controlling the "degree of order" (commonly known as the "fluidity") of membranes, which controls the activity of certain membrane-bound enzymes, membrane-bound receptors (for example hormones), etc.

Linoleic acid is an interesting special case since it forms part of the composition of acylceramides (ceramide whose fatty acid is an $\overline{\omega}$-hydroxylated fatty acid, this $\overline{\omega}$-OH group always being esterified with the COOH of a linoleic acid). By combining with the protein portion of corneocytes, these acylceramides play a dominant role in the barrier function of the epidermis (controlling water loss), and in limiting the penetration of cutaneous attacking factors. By way of example, type 1 ceramides are deficient in acne, atopic dermatitis and aging.

Thus, the food ingredient according to the invention contributes toward the recommended nutritional intake of linoleic acid, which is essential for the body when the natural plant oil is concentrated corn germ oil, concentrated sunflower oil and concentrated rapeseed oil.

Vitamin E

Tocopherols have variable vitamin activity depending on their form: the α (alpha) form known as vitamin E is the most active, especially for combating aging, photoaging and photoimmunosuppression since it is the most bioavailable in the membranes, the β (beta) and γ (gamma) forms having virtually no vitamin activity.

Vitamin E is a biological antioxidant of polyunsaturated fatty acids which acts mainly on the membranes and lipoproteins, by trapping free radicals. It helps toward preventing aging of the skin.

Other actions are cited for vitamin E:

intervention in the prevention of certain cancers, stimulation of the immune response in the elderly, reduction of the risk of cataracts and retardation of the progress of neurovegetative diseases.

Nutritional studies have shown that there is no severe deficiency or lack of vitamin E in the human diet, but that in certain cases, the intake may be less than the recommended daily intake (R.D.I.), i.e. 10 mg α T.E. per day.

The main food sources of vitamin E are plant oils. Table I compares the supply of vitamin E in various food plant oils. Most plant oils are naturally rich in vitamin E, sunflower oil and wheatgerm oil being favored sources.

To reach the R.D.I., it suffices to consume about 1 g to 1.5 g of the food according to the present invention or 5 g of wheatgerm oil or 15 g of sunflower oil per day.

TABLE I

Comparative supply of vitamin E in various plant oils, expressed as mg of α-tocopherol equivalent (or mg of vitamin E) per 100 kcal

| | mg vit E (mg α-T.E.)/ 100 g | mg vit E (mg α-T.E.)/ 100 kcal |
|---|---|---|
| Wheatgerm | 135-225 | 15-25 |
| Sunflower | 45-90 | 5-10 |
| Corn | 27-45 | 3-5 |
| Rapeseed | 13.5-27 | 1.5-3 |
| Soybean | 9-30 | 1-3 |

SOURCE: MANUEL DES CORPS GRAS (1992), ED TEC & DOC - LAVOISIER

Plant oils are the richest sources of vitamin E, and the food ingredient according to the present invention is 10 to 100 times more concentrated in vitamin E than the plant oils of major consumption: sunflower oil, rapeseed oil, soybean oil and corn oil; the food ingredient according to the present invention thus constitutes a particularly rich source of vitamin E.

Phytosterols

Phytosterols are natural plant constituents of human food which are present at a level of 0.1% to 0.5% in plant oils. The daily intake of total phytosterols is estimated at less than 500 mg, i.e. 200 to 300 mg on average.

Phytosterols, the major terpenic constituents of plant unsaponifiable materials, have a molecular structure similar to cholesterol with different configurations of the side chain. Phytosterols are only sparingly absorbed by the intestinal mucosa; thus, the absorption of dietary β-sitosterol represents only 5% of the intake.

The hypocholesterolemiant action of phytosterols has been known since the 1950s.

The hypothesis regarding the mechanism of action is as follows: the phytosterols induce a reduction in cholesterol absorption by competing with it for its solubilization in the micelles of bile salts in the intestine (jejunum). Another hypothesis proposed is the action of phytosterols on certain enzymes of lipid metabolism.

The vast majority of the studies performed on man and animals maintain the value of phytosterols in the prevention of hypercholesterolemia or as a means of controlling mild hypercholesterolemia.

Moreover, phytosterols act on the excretion of bile salts, which might explain their action in the prevention of colorectal cancers; this hypothesis requires further study.

It has also been mentioned that phytosterols induce a reduction in blood cholesterol (LDL) and a mild increase in the synthesis and excretion of endogenous cholesterol.

Phytosterols may be involved in other biological processes under study:

inhibition of cell proliferation, estrogen activity, antiviral activity.

All the nutritional studies performed on phytosterols demonstrate that a supplementation of 0.8 to 3 g/day (depending on the population and the intended objectives) of phytosterols reduces the total cholesterol and the LDL-cholesterol. No significant harmful effect is mentioned and no maximum safety dose is given for phytosterols.

Finally, the food ingredient according to the invention may have the nutritional benefit of supplying linoleic acid C18:2 (n-6) and linolenic acid C18:3 (n-3), which are essential fatty acids to the human body, and it is also a food source of oleic acid C18:1 (n-9). Regarding this point, the oil concentrated in unsaponifiable material used in the context of the present invention is substantially equivalent to the starting plant oil.

The food ingredient according to the invention also has the nutritional benefit of being a favored source of phytosterols, the hypocholesterolemiant role of which is nowadays recognized.

Finally, the food ingredient according to the invention is a food source concentrated in vitamin E, which covers the R.D.I. for this liposoluble vitamin.

Thus, the food ingredient according to the invention is not a food of major consumption, but rather a food ingredient whose nutritional impact is a supplementation of vitamin E and of phytosterols in the human diet.

Method

The natural plant oil chosen from palm olein, corn germ oil, sunflower oil and rapeseed oil, concentrated in unsaponifiable material, is preferably prepared according to the following procedure.

The natural food plant oil chosen from palm olein, corn germ oil, sunflower oil and rapeseed oil, obtained from a storage tank made of stainless steel or of inert material (for example enamel), stored under nitrogen, is pumped toward a continuous degasser. This machine is a thin-film evaporator of falling-film model. The aim of this operation is to eliminate, before the distillation, any traces of water and of dissolved gases (nitrogen, oxygen, carbon dioxide, etc.) in the material to be treated.

The degassed oil is then pumped toward the molecular distillation device. This machine uses a technology of centrifugal type and has a maximum distillation capacity of 180 kg per hour. The distillation chamber is composed of the following main elements:
- a conical circular rotor 90 cm in diamater,
- a coil for circulating demineralized water (condenser),
- two chutes for recovering the residue and the distillate,
- an induction-heating system,
- a vacuum bell-jar.

The vacuum unit is itself composed of a vane pump (primary vacuum) and an oil diffusion pump (molecular vacuum).

In the chamber under vacuum, the pre-degassed oil is distributed continuously with the aid of a feed line at the center of the rotor. By virtue of the centrifugal force exerted by the rotor (spinning plate), the degassed oil is uniformly distributed in the form of a film at the surface of the rotor.

The surface of the spinning plate is heated by induction, thus allowing instantaneous vaporization of the unsaponifiable fraction (light constituents) of the degassed oil. The vapors of unsaponifiable materials are immediately condensed with the aid of a water-cooled coil onto the walls of the bell jar, while the residue is entrained via a chute at the periphery of the rotor.

Finally, the process is controlled to maintain the nutritional qualities of the food according to the invention, in particular the unsaturated fatty acids, the vitamin E and the sterols.

EXAMPLES

Example 1

Preparation of Concentrated Plant Oils and Composition Thereof

Oils 1.1 to 1.4 were prepared by molecular distillation, the unsaponifiable material is vaporized at a temperature of 230° C., and under a high vacuum of $10^{-3}$ mHg. The heating time during the molecular distillation is extremely short, lasting about 1/10th of a second, thus avoiding the thermal degradation of the unsaponifiable fraction.

The distillate enriched in unsaponifiable material is cooled at the outlet of the distillation device and then stored under nitrogen, protected from light.

The distillate enriched in unsaponifiable material can undergo a deodorization step under vacuum (3 mmHg) with injection of 5% steam at 130° C. for 2 hours.

This deodorization step is of the same type as that performed during the refining of food plant oils. The deodorized distillate is then dried under nitrogen at 100° C. for one hour.

1.1. Sunflower Oil

1) Quality

This is a sunflower oil concentrated in unsaponifiable material by molecular distillation, which has a fluid appearance at room temperature (possible slight cloudiness). It is pale yellow and has a relatively mild odor.

The acid number of this oil is 6.0 mg KOH/g max and its peroxide number is 10 meq $O_2$ active/kg max.

2) Composition

A. Fatty acids

| Palmitic acid | C16 | 5 to 12% |
|---|---|---|
| Stearic acid | C18 | 1 to 10% |
| Oleic acid | C18' | 14 to 35% |
| Linoleic acid | C18'' | 55 to 75% |
| Linolenic acid | C18''' | <0.5% |
| TOTAL unsaturated fatty acids | | >70% |

B. Content of unsaponifiable material: 5 to 10 g/100 g
C. Content of sterols: >3.5 g/100 g
   Sterol composition: 40% to 65% β-sitosterol
   : <1% brassicasterol
D. Content of tocopherols: >800 mg/100 g
Tocopherol composition: >90% α-tocopherol 1.2. Rapeseed Oil 1) Quality This is a rapeseed oil concentrated in unsaponifiable material by molecular distillation, which has the appearance of a semi-fluid fat at room temperature, is pale yellow and has a relatively mild odor.

The acid number of this rapeseed oil is 6 mg KOH/g max and its peroxide number is 10 meq $O_2$ active/kg max.

2) Composition

A. Fatty acids

| Palmitic acid | C16 | 3 to 8% |
|---|---|---|
| Stearic acid | C18 | 0.8 to 2.5% |
| Oleic acid | C18' | 50-70% |
| Linoleic acid | C18'' | 15 to 28% |
| Linolenic acid | C18''' | 6 to 14% |
| Erucic acid | C22' | <5% |
| TOTAL unsaturated fatty acids | | >75% |

B. Content of unsaponifiable material: 7 to 11 g/100 g
C. Content of sterols: >5 g/100 g
   Sterol composition 40% to 61% β-sitosterol
   : >5% brassicasterol
D. Content of tocopherols: >800 mg/100 g
Tocopherol composition: >30% to 50% α-tocopherol 1.3. Corn Germ Oil 1) Quality This is a corn germ oil concentrated in unsaponifiable material by molecular distillation, which has a fluid appearance at room temperature possibly with crystals in suspension. It is golden yellow and has a relatively mild odor.

The acid number of the corn germ oil is 6.0 mg KOH/g max and its peroxide number is 10.0 meq $O_2$ active/kg max.

2) Composition

A. Fatty acids

| Palmitic acid | C16 | 10 to 20% |
|---|---|---|
| Stearic acid | C18 | <3.3% |
| Oleic acid | C18:1 | 20.0 to 42.2% |
| Linoleic acid | C18:2 | 34.0 to 65.6% |
| α-Linolenic acid | C18:3 | <2.0% |
| TOTAL unsaturated fatty acids | | >70.0% |

B. Content of unsaponifiable material: 9 to 15 g/100 g
C. Content of sterols: >7 g/100 g
   Sterol composition: 55.0% to 66.0% β-sitosterol
   : <1% brassicasterol
D. Content of tocopherols: ≧1300 mg/100 g
Tocopherol composition: 68.0% to 89% γ-tocopherol 1.4. Palm Olein 1) Quality This is a palm olein concentrated in unsaponifiable material by molecular distillation, which has the appearance of a cream-colored grease at room temperature, of mild odor.

The acid number of this palm olein is 6.0 mg KOH/g max and its peroxide number is 10.0 meq $O_2$ active/kg max.

2) Composition
A. Fatty acids

| Palmitic acid | C16 | 39.0 to 47.5% |
| Stearic acid | C18 | 3.5 to 6.0% |
| Oleic acid | C18:1 | 36.0 to 44.0% |
| Linoleic acid | C18:2 | 9.0 to 12.0% |
| α-Linolenic acid | C18:3 | <0.5% |
| TOTAL unsaturated fatty acids | | >50.0% |

B. Content of unsaponifiable material: 5 to 10 g/100 g
C. Content of sterols,
triterpenic alcohols and
methyl sterols: >2 g/100 g
   Sterol composition: 50.0 to 62.0% β-sitosterol
   :<1% brassicasterol
D. Content of tocopherols and tocotrienols: >1000 mg/100 g
Content of tocopherols: >300 mg/100 g
Tocopherol composition: >80% α-tocopherol
Content of tocotrienols: >700 mg/100 g
Tocotrienol composition: >45.0% γ-tocotrienol Example 2

Examples of Food Use of the Concentrated Plant Oils of the Invention 2.1. Preparation of Cookies Containing 2% and 10.6% Sunflower Oil Concentrated in Unsaponifiable Material Shortbread Preparation Process A. Formula

|  | 2% Preparation | | 10.6% Preparation | |
| --- | --- | --- | --- | --- |
| Flour | 1500 | 62.5 | 1500 | 62.5 |
| Margarine | 207 | 8.6 | 0 | 0 |
| Sunflower oil* | 48 | 2.0 | 255 | 10.6 |
| Sugar | 297 | 12.4 | 297 | 12.4 |
| Milk powder | 30 | 1.3 | 30 | 1.3 |
| Salt | 9 | 0.4 | 9 | 0.4 |
| Water | 255 | 10.6 | 255 | 10.6 |
| Baking powder | 9 | 0.4 | 9 | 0.4 |
| Whole egg | 45 | 1.9 | 45 | 1.9 |
| TOTAL | 2400 | 100 | 2400 | 100 |

*concentrated sunflower oil of example 1.1.

B. Procedure

The concentrated sunflower oil and the margarine are placed at 20° C. in a stainless-steel kneading bowl and are mixed for one minute at a speed of 75 rpm. The salt, the sugar, the egg, the baking powder and the flour are added; the mixture is mixed for 5 minutes at a speed of 75 rpm. The water is added at 20° C. and the mixture is mixed for 3 minutes at a speed of 75 rpm.

The dough thus obtained is divided into cookies, which are then placed on a metal tray. The cookies are baked in a ventilated oven at 160° C. for 11 minutes.

The cookie containing 2% concentrated sunflower oil is enriched with 20 mg/100 g of native vitamin E and 100 mg/100 g of native phytosterols from the starting sunflower oil.

The cookie containing 10.6% concentrated sunflower oil is enriched with 100 mg/100 g of native vitamin E and with 530 mg/100 g of native phytosterols from the starting sunflower oil.

2.2. Preparation of Cookies Containing 2% and 10.6% Rapeseed Oil Concentrated with Unsaponifiable Material Creaming Process A. Formula

|  | 2% Preparation | | 10.6% Preparation | |
| --- | --- | --- | --- | --- |
| Flour | 1500 | 62.5 | 1500 | 62.5 |
| Margarine | 207 | 8.6 | 0 | 0 |
| Rapeseed oil* | 48 | 2.0 | 255 | 10.6 |
| Sugar | 297 | 12.4 | 297 | 12.4 |
| Milk powder | 30 | 1.3 | 30 | 1.3 |
| Salt | 9 | 0.4 | 9 | 0.4 |
| Water | 255 | 10.6 | 255 | 10.6 |
| Baking powder | 9 | 0.4 | 9 | 0.4 |
| Whole egg | 45 | 1.9 | 45 | 1.9 |
| TOTAL | 2400 | 100 | 2400 | 100 |

*concentrated rapeseed oil of example 1.2.

B. Procedure

The concentrated rapeseed oil and the margarine are placed at 20° C. in a stainless-steel kneading bowl and are mixed for one minute at a speed of 75 rpm. The salt, the sugar and the egg are added: the mixture is mixed for one minute at a speed of 102 rpm.

Water is added at 40° C. in two portions: the mixture is mixed until a homogeneous cream is obtained at a speed of 102 rpm, and the flour and baking powder are added; the mixture is mixed for one minute at a speed of 75 rpm.

The dough thus obtained is divided into cookies and then placed on a metal tray. The cookies are baked in a ventilated oven at 160° C. for 11 minutes.

The cookie containing 2% concentrated rapeseed oil is enriched with 10 mg/100 g of native vitamin E and 140 mg/100 g of native phytosterols from the starting rapeseed oil, and 160 mg/100 g of linolenic fatty acid (C18:3 n-3 or ω3).

The cookie containing 10.6% concentrated rapeseed oil is enriched with 50 mg/100 g of native vitamin E and with 740 mg/100 g of native phytosterols from the starting rapeseed oil, and 850 mg/100 g of linolenic fatty acids (C18:3 n-3 or ω3).

2.3. Preparation of a Salad Dressing Containing 2% and 10% of Sunflower Oil Concentrated in Unsaponifiable Material Pasteurized Vacuum Process A. Formula

|  | 2% Preparation |  | 10% Preparation |  |
|---|---|---|---|---|
| Plant oil | 480 |  | 400 |  |
|  |  | 48 |  | 40 |
| Sunflower oil* | 20 | 2 | 100 | 10 |
| Serum protein | 10 | 1 | 10 | 1 |
| Alcohol vinegar | 55 | 5.5 | 55 | 5.5 |
| Mustard | 40 | 4 | 40 | 4 |
| Pepper | 1 | 0.1 | 1 | 0.1 |
| Salt | 10 | 1 | 10 | 1 |
| Sorbate | 1 | 0.1 | 1 | 0.1 |
| Starch | 20 | 2 | 20 | 2 |
| Xanthan-guar | 2.5 | 0.25 | 2.5 | 0.25 |
| Water | 360.5 | 36.05 | 360.5 | 36.05 |
| TOTAL | 1000 | 100 | 1000 | 100 |

*concentrated sunflower oil of example 1.1.

B. Procedure

The powders (serum protein, pepper, salt, sorbate, starch and xanthan-guar) are introduced into a stainless-steel mixing vessel; the mixture is mixed with water for one minute at 1500 rpm under vacuum.

The sunflower oil concentrate and sunflower oil are introduced into the preparation in 4 portions, at a rate of one dose per minute. The vinegar and mustard are introduced: the mixture is mixed for 20 seconds.

The salad dressing is packaged hermetically and pasteurized in a water bath for 2 hours at 80°C.

The salad dressing containing 2% concentrated sunflower oil is enriched with 20 mg/100 g of native vitamin E and 100 mg/100 g of native phytosterols from the starting sunflower oil.

The salad dressing containing 10% concentrated sunflower oil is enriched with 100 mg/100 g of native vitamin E and with 500 mg/100 g of native phytosterols from the starting sunflower oil.

2.4. Preparation of a Salad Dressing Containing 2% and 10% Rapeseed Oil Concentrate Pasteurized-air or Sterilized or Frozen Process A. Formula

|  | 2% Preparation |  | 10% Preparation |  |
|---|---|---|---|---|
| Plant oil | 480 | 48 | 400 | 40 |
| Rapeseed oil* | 20 | 2 | 100 | 10 |
| Serum protein | 10 | 1 | 10 | 1 |
| Alcohol vinegar | 55 | 5.5 | 55 | 5.5 |
| Mustard | 40 | 4 | 40 | 4 |
| Pepper | 1 | 0.1 | 1 | 0.1 |
| Salt | 10 | 1 | 10 | 1 |
| Sorbate | 1 | 0.1 | 1 | 0.1 |
| Pregel starch 126 16 | 20 | 2 | 20 | 2 |
| Xanthan-guar CX 391 | 2.5 | 0.25 | 2.5 | 0.25 |
| Water | 360.5 | 36.05 | 360.5 | 36.05 |
| TOTAL | 1000 | 100 | 1000 | 100 |

*concentrated sunflower oil of example 1.1.

B. Procedure

The powders (serum protein, pepper, salt, sorbate, pregel starch, xanthan-guar) are introduced into a stainless-steel mixing vessel; the mixture is mixed with the water for one minute at 1500 rpm under air.

The concentrated rapeseed oil and the plant oil are introduced into the preparation in 4 portions, at a rate of one dose per minute. The vinegar and mustard are introduced: the mixture is mixed for 20 seconds.

The salad dressing is packaged and then pasteurized in a water bath for 2 hours at 80° C. or sterilized in a rotary autoclave for 40 minutes at 112° C. or frozen in a freezer chest at −18° C.

The salad dressing containing 2% concentrated rapeseed oil is enriched with 10 mg/100 g of native vitamin E and with 140 mg/100 g of native phytosterols from the starting rapeseed oil and with 160 mg/100 g of linolenic fatty acid (C18:3 n-3 or ω3).

The salad dressing containing 10% concentrated rapeseed oil is enriched with 50 mg/100 g of native vitamin E and with 700 mg/100 g of native phytosterols from the starting rapeseed oil, and 800 mg/100 g of linolenic fatty acid (C18:3 n-3 or ω3).

The concentrated plant oils according to the present invention, used as food ingredients, and also the food compositions and food supplements containing this concentrated plant oil according to the invention, have hypocholesterolemiant properties, act in preventing certain cancers and cardiovascular diseases, in stimulating the immune response in the elderly, in reducing the risk of cataracts and in retarding the prgress of neurovegetative diseases, and also in preventing aging of the skin, photoaging and photoimmunosuppression.

The invention claimed is:

1. A food composition or supplement comprising a fraction of sunflower oil enriched with unsaponifiables, wherein said fraction contains:
   a) from 0.2% to 10% by mass of sterols, triterpene alcohols and methylsterols,
   b) from 0.1% to 2% by mass of total tocopherols and tocotrienols,
   c) from 0.1% to 7% by mass of squalene,
   d) from 0.1% to 1% by mass of carotenes;
   and wherein the fraction has an acid number of 6 mg KOH/g max and a peroxide number of 10 meq $O_2$ active/kg max.

2. The food composition or supplement of claim 1, wherein the fraction comprises from 0.5% to 1.5% tocopherol and from 1.3% to 8% phytosterol.

3. The food composition or supplement of claim 1, containing from 0.5% to 20% by mass of the fraction of sunflower oil.

4. The food composition or supplement of claim 1, containing from 10% to 100% by mass of the fraction of sunflower oil.

5. A method for improving the appearance of the skin, comprising orally administering to a subject in need thereof an effective amount of the food composition or supplement of claim 1.

6. A method for treating inflammation comprising orally administering to a subject in need thereof an effective amount of the food composition or supplement of claim 1.

* * * * *